US00PP20272P2

(12) United States Plant Patent
Sturdza

(10) Patent No.: US PP20,272 P2
(45) Date of Patent: Sep. 8, 2009

(54) ***HYDRANGEA* PLANT NAMED 'LE VASTERIVAL'**

(50) Latin Name: *Hydrangea paniculata*
Varietal Denomination: Le Vasterival

(75) Inventor: Greta Sturdza, Varengeville sur Mer (FR)

(73) Assignee: Pepinieres Minier, SA, Beafort En Callos (FR)

( * ) Notice: Subject to any disclaimer, the term of this patent is extended or adjusted under 35 U.S.C. 154(b) by 0 days.

(21) Appl. No.: 12/215,945

(22) Filed: Jul. 1, 2008

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant VAriety Database Jun. 2008. p. 1.*

* cited by examiner

*Primary Examiner*—Annette H Para
(74) *Attorney, Agent, or Firm*—Penny J. Aguirre

(57) ABSTRACT

A new cultivar of *Hydrangea pauiculata* named 'Le Vasterival' that is characterized by its panicles that are held nearly upright and rounded in form, its white star-shaped sterile flowers with sepals that are elliptic in shape and curl inward when mature, its bright green slightly rugose foliage, its continuous blooming habit from mid July to late September, and its outwardly arching plant habit.

2 Drawing Sheets

Genus/species: *Hydrangea paniculata.*
Varietal denomination: 'Le Vasterival'.

BACKGROUND OF THE INVENTION

The present invention relates to a new and distinct cultivar of *Hydrangea paniculata* and will be referred to hereafter by its cultivar name, 'Le Vasterival'. 'Le Vasterival' represents a new panicle *hydrangea*, a deciduous shrub grown for landscape use.

'Le Vasterival' was discovered by the inventor in Varengeville Sur Mer, France in summer of 2003. 'Le Vasterival' arose as a naturally occurring branch mutation on an unnamed seedling of *Hydrangea paniculata* 'Floribunda' (both the seedling and 'Floribunda' are un patented).

Asexual reproduction of the new cultivar was first accomplished by softwood stem cuttings in Beaufort en Vallée in winter of 2004 under the direction of the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Le Vasterival' as a unique cultivar of *Hydrangea paniculata.*

1. 'Le Vasterival' exhibits unique sterile flowers that have white sepals that are elliptic in shape, a cuneate base, and that curl inward when mature.
2. 'Le Vasterival' exhibits panicles that are held nearly upright and are nearly round in overall form.
3. 'Le Vasterival' exhibits leaves with a slightly rugose and slightly pubescent surface.
4. 'Le Vasterival' blooms continuously from mid July to late September in France.
5. 'Le Vasterival' exhibits an outwardly arching plant habit.

The new cultivar of *Hydrangea* differs from its parent plant, a seedling of 'Floribunda', in having leaves with a more rugose and pubescent surface, more rounded inflorescences, unique sterile sepal shape, and in having a longer blooming period. 'Le Vasterival' can be compared to the cultivar 'Barbara' (U.S. Plant Pat. No. 13,606), which is similar in blooming period and inflorescence color but differs from 'Barbara' in sterile sepal shape, in having panicles that are less rounded in shape, and in having a more arching plant habit. 'Le Vasterival' can also be compared to 'White Moth' (not patented), which has a similar plant habit and in having upright and rounded panicles, however 'Le Vasterival' differs from 'White Moth' in having sterile sepals that differ in shape and are larger in size and in having inflorescences that are larger in size.

BRIEF DESCRIPTION OF THE DRAWINGS

The accompanying photographs were taken of a plant and plant parts of a five year-old plant of 'Le Vasterival' as grown outdoors in a trial garden in Beaufort en Vallée, France.

The photograph in FIG. 1 illustrates a plant of 'Le Vasterival' in bloom.

Figure 1:
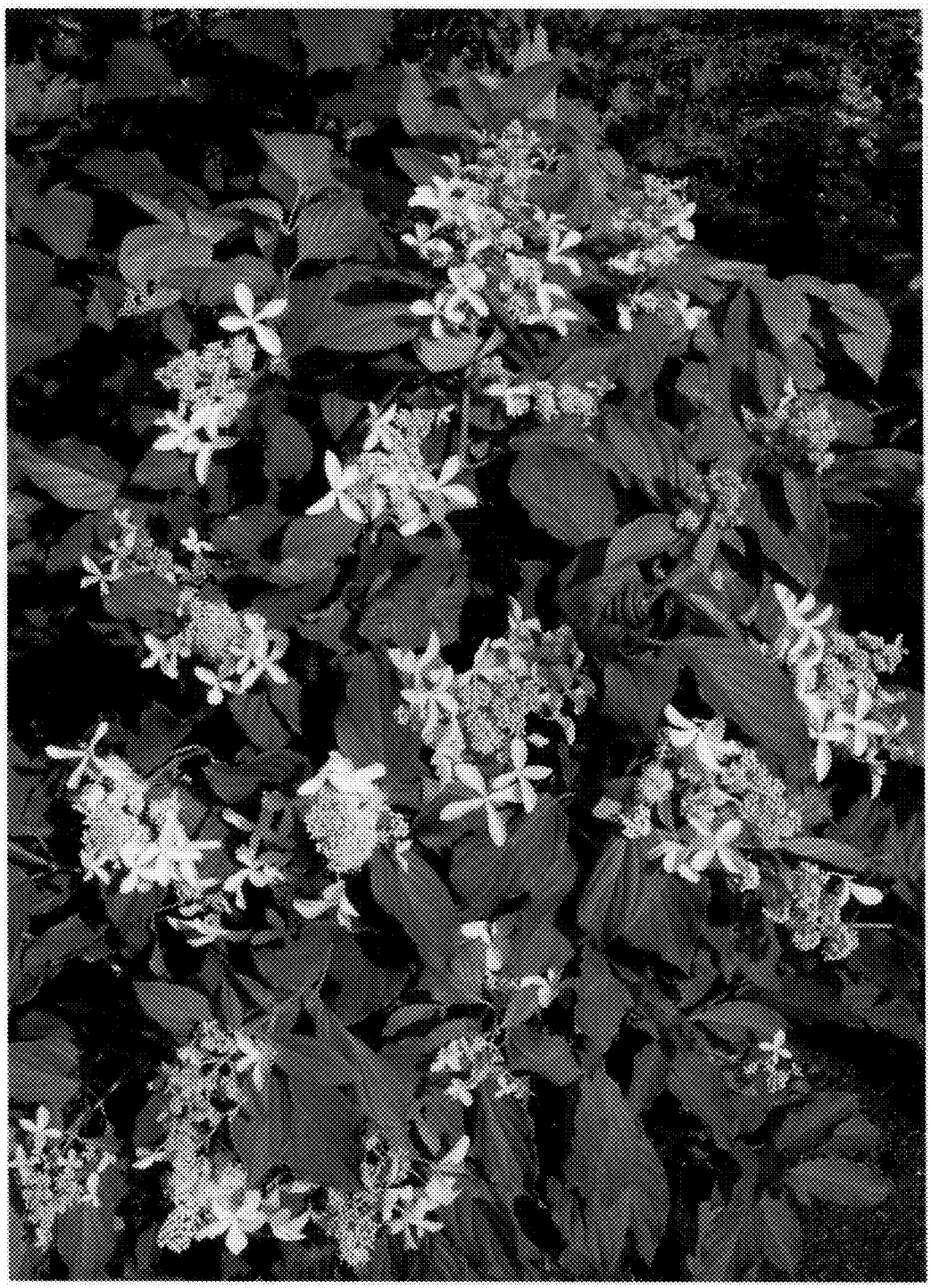
Figure 2:
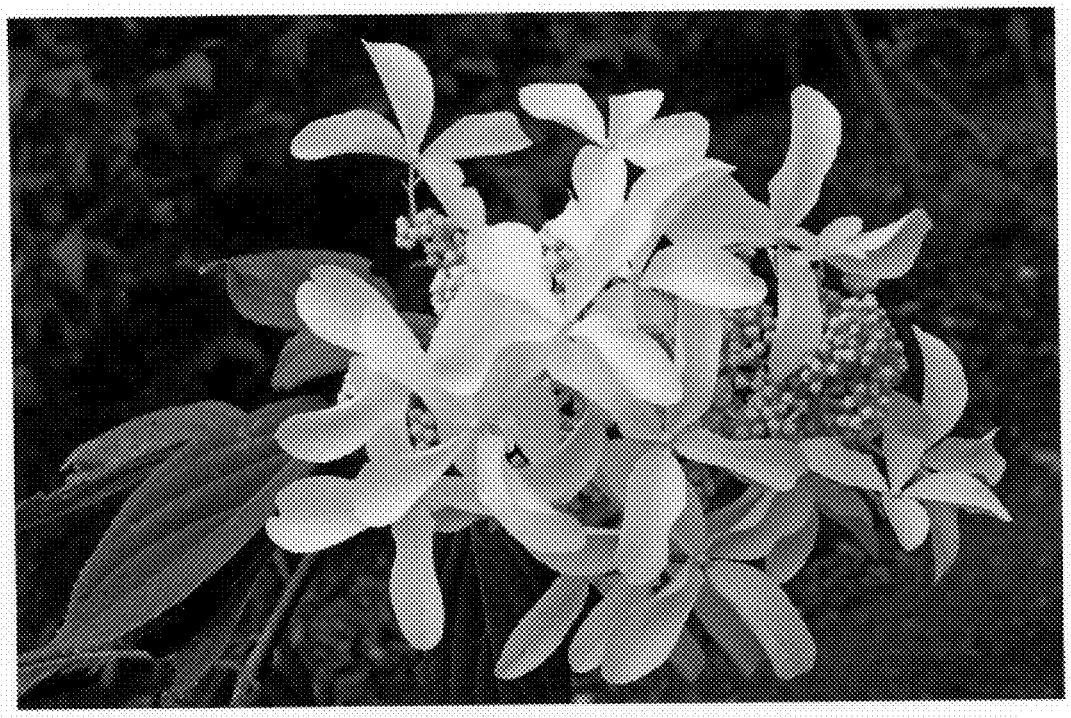

The photograph in FIG. 2 provides a close-up view of a fully open inflorescence.

Figure 3:
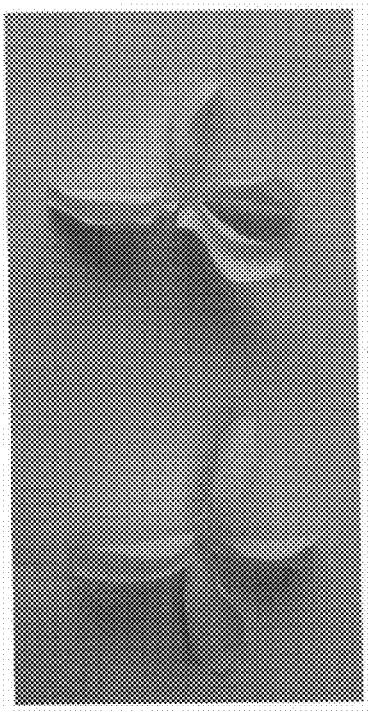

The photograph in FIG. 3 provides a close-up view of 2 flowers of 'Le Vasterival'.

Figure 4:
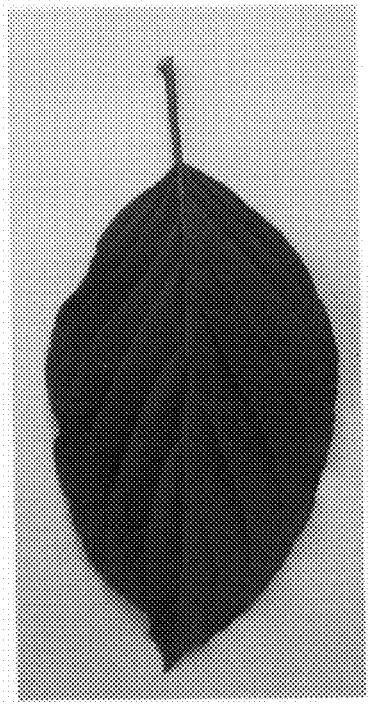

The photograph in FIG. 4 provides a close-up view of a leaf of 'Le Vasterival'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of five year-old plants of the new cultivar as grown outdoors in a trial garden in Beaufort en Vallée, France. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

General description:

*Blooming period.*—Blooms continuously from mid July to late September in France.

*Plant habit.*—Outwardly arching.

*Height and spread.*—Reaches about 2 m in height and 3 m width when mature.

*Hardiness.*—U.S.D.A. Zones 3 to 8.

*Diseases.*—No susceptibility or disease resistance has been observed.

*Root description.*—Fibrous.

*Growth rate.*—Vigorous.

Stem description:

*Stem shape.*—Round, solid.

*Stem strength.*—Strong.

*Stem color.*—197A in color.

*Stem size.*—Average of 1.5 m (to base of inflorescence) in length, average of 5 mm in width.

*Stem surface.*—Glabrous, rough.

*Internode length.*—Average of 5 cm.

*Branching.*—A single dormant stem will produce an average of 4 lateral branches, sublateral branching is determined by pinching; 2 stems develop per pinched node.

Foliage description:

*Leaf shape.*—Elliptic.

*Leaf arrangement.*—Opposite.

*Leaf division.*—Simple.

*Leaf base.*—Cuneate.

*Leaf apex.*—Acute.

*Leaf margins.*—Entire with rough hairs.

*Leaf venation.*—Penninerved, recessed on upper surface, color 144B on upper surface and lower surface.

*Leaf size.*—Average of 17 cm in length and 8 cm in width.

*Leaf attachment.*—Petiolate.

*Leaf surface.*—Slightly rugose and slightly pubescent.

*Leaf color.*—Upper and lower surfaces 144A to 137A.

*Petioles.*—Average of 2 cm in length and 3 mm in width, 166B in color, glabrous surface.

Inflorescence description:

*Inflorescence type.*—Terminal panicles in a nearly rounded form comprised of star-shaped sterile flowers atop a mound of fertile flowers.

*Lastingness of inflorescence.*—Persistent but color is retained for about 4 weeks.

*Inflorescence number.*—One per lateral or sublateral stem if pinched.

*Inflorescence size.*—Average of 19 cm in height and 17 cm in diameter.

*Flower number.*—Numerous, average of 17 sterile flowers and about 200 fertile flowers per inflorescence.

*Flower fragrance.*—None.

*Flower aspect.*—Upright to stem.

*Flower size.*—Sterile flowers; average of 8 cm in diameter and 2.3 cm in depth, fertile flowers; average of 4.5 mm in diameter and 6 mm in depth.

*Flower buds* (*sterile flowers*).—Average of 4 mm in length and 3 mm in width, globose in shape, 157D in color, glabrous surface.

*Peduncles.*—Strong, average of 10 cm in length and 1 mm in width 144C in color and 166B when young, surface is glabrous.

*Pedicels* (*sterile flowers*).—Moderate strength, average of 5 mm in length and 1 mm in width, 145D to 155A in color, surface is glabrous and shiny.

*Color of fertile flowers.*—155A.

*Sepals* (*sterile flowers*).—4, un-fused, rotate in arrangement, glabrous on both surfaces elliptic in shape on sterile flowers, aspect is curled inward when mature, entire margin, apex is irregular but typically rounded and some are notched, average of 4 cm in length and 2.6 cm in width, color upper and lower surface; 145C, color on when fully open flower on both surfaces; 155A, color of both surfaces in autumn; 145C.

Reproductive organs: (fertile flowers):

*Stamens.*—Average of 10, anther is about 1 mm in length and 165A in color, filament is an average of 4 mm in length and 155A in color, pollen was not observed.

*Pistils.*—Average of 3, average of 2 mm in length, 165A in color, style is an average of 1.5 mm in length and 155A in color.

Fruit and seed.—Was not observed on the plants available for data collection.

It is claimed:

1. A new and distinct cultivar of *Hydrangea* plant named 'Le Vasterival' substantially as herein illustrated and described.

* * * * *